United States Patent [19]
Nyman

[11] Patent Number: 5,507,662
[45] Date of Patent: Apr. 16, 1996

[54] DEVICE FOR AFFIXING AN ELECTRODE CABLE TO AN APPARATUS

[75] Inventor: Per Nyman, Djursholm, Sweden

[73] Assignee: Siemens Elema AB, Solna, Sweden

[21] Appl. No.: 252,245

[22] Filed: Jun. 1, 1994

[30] Foreign Application Priority Data

Jun. 1, 1993 [SE] Sweden .................................. 9301856

[51] Int. Cl.$^6$ ..................................................... H01R 4/50
[52] U.S. Cl. ............................ 439/348; 439/819; 439/868
[58] Field of Search ......................... 607/122, 37, 116, 607/126, 38; 439/675, 840, 841, 868, 883, 668, 669, 909, 810–814, 348, 817–819

[56] References Cited

U.S. PATENT DOCUMENTS

| 4,764,132 | 8/1988 | Stutz, Jr. ................................. 439/810 |
| 4,784,141 | 11/1988 | Peers-Trevarton . |
| 4,913,147 | 4/1990 | Fahlstrom et al. . |
| 4,936,366 | 6/1990 | Truex et al. . |
| 5,007,864 | 4/1991 | Stutz, Jr. ................................. 439/814 |
| 5,086,773 | 2/1992 | Ware . |
| 5,304,219 | 4/1994 | Chernoff et al. ........................ 439/675 |

FOREIGN PATENT DOCUMENTS 0339877  11/1989  European Pat. Off. .
0448760  10/1991  European Pat. Off. .
2518571  10/1975  Germany .

Primary Examiner—David L. Pirlot
Attorney, Agent, or Firm—Hill, Steadman & Simpson

[57] ABSTRACT

A device for affixing an electrode cable to an apparatus is disclosed, suitable for affixing an electrode cable for use in vivo to an implantable medical apparatus for emitting electrical pulses, such as a pacemaker or a defibrillator, wherein the electrode cable has a pin-like proximal end. The apparatus is provided with a connector part at which the affixing device is located to mate with the proximal end of the electrode cable. The affixing device includes a spring element which is disposed substantially perpendicularly to the longitudinal axis of the proximal end of the electrode cable when the proximal end is contained in the connector part. The spring element carries clamping elements, and the spring element is movable between first and second positions. When the spring element is in the first position, the clamping elements are caused to be disposed so as to permit the proximal end of the electrode cable to pass the clamping elements, and when the spring element is in the second position, the clamping elements are caused to engage the proximal end of the electrode cable to affix the proximal end in the connector part. The affixing device has a simple structure, which is inexpensive to manufacture, and which is simple to handle during implantation while still providing good and reliable electrical contact between the electrode cable and the apparatus.

11 Claims, 3 Drawing Sheets

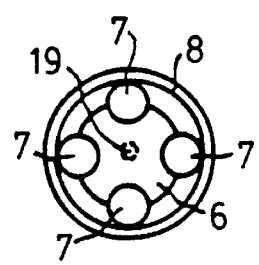
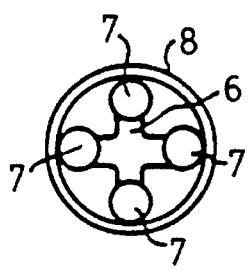
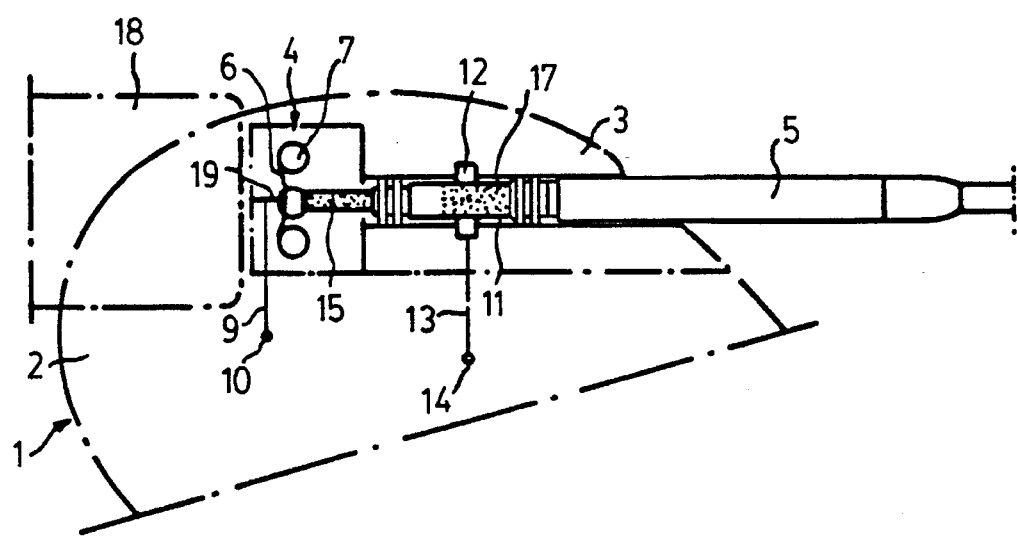

DEVICE FOR AFFIXING AN ELECTRODE CABLE TO AN APPARATUS

BACKGROUND OF THE INVENTION

1. Field of the Invention

The present invention is directed to a device for affixing an electrode cable to an apparatus for emitting electrical pulses, and in particular to an electrode cable for use in vivo with an implantable medical apparatus such as a pacemaker or a defibrillator, wherein the electrode cable is of the type having a pin-like proximal end and wherein the apparatus is of the type having a connector part, which contains the affixing device, for receiving and holding the pin-like proximal end of the electrode cable.

2. Description of the Prior Art

An affixing device of the type generally described above is disclosed in German OS 2 518 571. This device is for connecting at least one pacemaker electrode to a pacemaker. The affixing device includes a screw, disposed perpendicularly to the longitudinal axis of the electrode cable when the cable is contained in the connector, the screw being screwed into the connector part from the top side of the connector part to affix the electrode cable at a point on the distal end thereof. To prevent body fluids from penetrating into the connector part, the opening for the screw is provided with a sealing plug. By means of the use of a screw and a sealing plug, the connector part is relatively tall, which is undesirable in view of the goal of achieving a pacemaker having a smallest possible size. Moreover, this known affixing device presents problems for the implanting physician in securing the electrode cable to the pacemaker. To ensure that the screw which affixes the electrode cable has been sufficiently tightened, but without damaging the coupling site, tightening is performed with a special screwdriver which is designed to snap (break) or at least partially fracture, once the desired torque value has been achieved. The sealing plug is then applied by means of another special tool. This makes connecting the electrode cable to the pacemaker an relatively intricate procedure for the physician. Moreover, the affixing procedure occurs in conjunction with implantation of the electrode cable and the pacemaker. This means that the distal end of the electrode cable has already been introduced into the venous system of the patient, and placed, for example, in the heart just prior to the time that the electrode cable is to be connected to the pacemaker. Since the electrode cable has already been implanted, this limits the freedom of movement which is available to the physician for manipulating the electrode cable during the procedure for affixing the proximal end of the electrode cable to the pacemaker. Another disadvantage associated with this known device is that it is awkward to release the electrode cable from the pacemaker by reversing the affixing process, which may be necessary if the electrode cable is defective, or become defective over time, or if the pacemaker battery must be replaced. Separating the electrode cable from the pacemaker is not easy given this known affixing device.

A so-called "black hole"-type pacemaker coupling is described in U.S. Pat. No. 4,913,147. In this type of pacemaker coupling, the proximal end of the electrode cable is affixed to the pacemaker and seals the affixing area without the use of screws and sealing plugs. This is accomplished either using a spring, which is provided in the pacemaker connector socket and which can engage the pin-like proximal end of the electrode cable perpendicularly to the longitudinal axis of the pin, or using a ring attached to the pacemaker connector socket and through which the pin-like cable end is inserted. The ring alters its shape following insertion of the proximal cable end into the connector socket, so as to clamp and affix the proximal end of the cable in the connector socket. Both the spring and the ring are made of a metal alloy which has a shape at a first temperature which permits entry of the proximal end of the electrode cable into the pacemaker connector socket and which changes shape at a second temperature (body temperature in this instance) to affix the electrode cable end in the desired manner. A disadvantage of this known type of electrode affixing device is that the electrode cable cannot be reliably coupled to the pacemaker until the pacemaker and the electrode have been implanted, i.e., when the spring or the ring has reached the body temperature.

Another "black hole"-type pacemaker coupling is disclosed in European Application 0 048 760. In this known coupling, electrode connection is also achieved without the aid of screw fasteners or sealing plugs. This known pacemaker coupling includes a helical spring which is coaxially arranged on the proximal end of the electrode cable which is introduced into the connector socket. The helical spring extends along a part of the length of the cable socket. The proximal end of the electrode cable is clamped in the connector socket by flanges carried on sleeves which surround the helical spring when the proximal end is inserted into the connector part. The inner diameter of the helical spring is somewhat smaller than the outer diameter of the proximal end of the electrode cable which is to be connected to the pacemaker. When the electrode end is affixed, this end is introduced partially into the screw helical spring and is simultaneously rotated in a direction counter to the coil direction of the helical spring, so that the helical spring expands as the proximal end of the electrode cable is advanced into the connector socket. When the electrode end is completely inserted, the spring bias causes the helical spring to try to resume its original dimensions, thereby applying pressure to affix the proximal end of the electrode cable. The pacemaker connector socket also includes a connector part which is separate from the helical spring. This known pacemaker coupling thus has a relatively complicated structure and if the aforementioned rotation of the electrode end required for completing the coupling does not occur, the electrical contact surface on the electrode end, and even the helical spring in the pacemaker socket, may be destroyed.

SUMMARY OF THE INVENTION

It is an object of the present invention to provide an affixing device for affixing the proximal end of an electrode cable to an apparatus which emits electrical energy, which has a simple structure, is inexpensive to manufacture, and which can be operated in a simple manner while simultaneously providing good affixing of the electrode cable. It is a further object of the present invention to provide such an affixing device which achieves reliable electrical contact between the electrode cable and the apparatus.

This above object is achieved in accordance with the principles of the present invention in an affixing device for an electrode cable having a pin-like proximal end, the affixing device being disposed in the connector part of the apparatus, and having a spring element disposed substantially perpendicularly to the longitudinal axis of the proximal end of the electrode cable to be affixed. The spring element is provided with clamping elements for affixing the proximal end of the electrode cable in the connector part. The spring element is movable between first and second positions, the first position of the spring element causing the clamping elements to assume a position or shape which permits the proximal end of the electrode cable to pass the clamping elements. In the second position, the clamping elements are caused to engage and affix the proximal end of the electrode cable. Affixing of the pin-like end of the electrode cable is thus achieved in accordance with the invention merely by introducing this end into the connector part of the electrical apparatus, without any torsional action. The pressure fixing of the cable end in the connector part by means of the clamping elements is at least as effective as fixing with a screw. A very simple structure of the affixing device of the invention is achieved in an embodiment wherein the change between the first and second positions of the spring element is produced with the aid of a magnet. Depending on the causing the spring element to move from said first position to said second position with the aid of a magnet. Depending upon the parts of the affixing device to be activated, the spring element and/or the clamping elements can be made of a material susceptible to magnetic force.

In a preferred embodiment of the invention, the spring element is a convex disk. In the first position, the bulge of the convex disk faces the proximal end of the electrode cable, and in the second position the bulge faces away from the proximal end. As a result of this shape, the spring element can serve as a sound emitter, because it emits an audible click when it snaps from one position into the other. When the convex disk is in the first position, the electrode cable can be introduced into the connector part so that the proximal end thereof passes the clamping elements, at least partially, until the end of the pin reaches the disk. When the electrode end is pressed against the disk so the bulge is deformed, the disk snaps into the second position, in which the bulge faces away from the end of the electrode cable. This caused the clamping element to be activated and displaced so as to apply pressure to affix the end of the electrode cable in the connector part. The clicking sound achieved in this way confirms that the end of the electrode is affixed to the apparatus.

The change in position of the spring element can alternatively be achieved with a magnet, as mentioned above, which is applied in a special manner described below. When the electrode cable is to be separated from the apparatus, the convex disk can be activated using the magnet so that it again assumes the aforementioned first position, in which the proximal end of the electrode cable can be detached from the affixing device. The physician will again hear a clicking sound emitted by the convex disk, confirming that the end of the electrode cable has become detached from affixing device, and thus the electrode cable can be removed from the apparatus.

In a simple version of the invention, the profile of the spring element is V-shaped, such that the inner diameter of the clamping elements is smaller than the outer diameter of the pin-like proximal end of the electrode cable. Before the end of the electrode cable is introduced into the affixing device, the arms of the V are spread by means of the aforementioned magnet, and the magnet is removed after the electrode end has been introduced in the prescribed manner. The spring element then returns to its original shape together with the clamping elements, which can be arranged to advantage at the free ends of the arms of the V. The clamping elements thereby exert pressure onto the pin-like proximal end of the electrode cable, thereby affixing the electrode cable in the connector part. When the end of the electrode cable is to be separated from the apparatus, the magnet again acts on the V-shaped arms of the spring element, so that the clamping elements disengage from the surface of the electrode end.

In a further version of the invention, the clamping elements are evenly distributed on the spring element around the proximal end of an electrode cable to be held in the affixing device. In this manner, the end of the electrode cable is optimally affixed within the connector part of the apparatus.

In another version of the invention, which is structurally simple, the clamping elements are spherical. This significantly facilitates mounting of the clamping elements on the spring element, because it does not matter which part of the surface of the clamping elements must face the end of the electrode cable for the purpose of engaging and affixing that end. Moreover, as a result of their spherical shape, the clamping elements have a relatively large material mass, thereby increasing the attractive force exerted by the magnet on the clamping elements if the spheres are made of a material susceptible to magnetic force.

In a further embodiment of the invention, clamping elements are electrically coupled to an electrical contact in the apparatus. This provides highly reliable electrical contact between the proximal end of the electrode cable and the apparatus.

In another preferred embodiment of the invention, the affixing device is contained in a hood-shaped, truncated cone, having a base which is attached to the apparatus. The maximum diameter of the hood is only slightly larger than the outer dimension of the spring element in the extended (first) position. The slope of the inner wall of the truncated cone is selected so that it roughly follows a curve describing the peripheral surface of the fixing element when the fixing element moves from the first position to the second position. In this manner, the fixing device is held within the hood without being physically attached to the hood, thereby making it easy to mount the affixing device in the connecting part of the apparatus.

In another structurally simple version of the invention, a middle area on a side of the spring element which faces the apparatus is permanently connected to the apparatus. This embodiment can be employed instead of the above-described hood for fastening the spring element in the connector part.

DESCRIPTION OF THE DRAWINGS

FIG. 3 is a cross-section of the affixing shown in FIG. 2, taken along line III—III.

FIG. 4 is a cross-section of the affixing device shown in FIG. 2, taken along line III—III, but provided with a different shape than the shape shown in FIG. 3.

FIGS. 5, 6 and 7 respective show side schematic views of a connector part of an apparatus for emitting electrical pulses, with different embodiments of an affixing device constructed in accordance with the principles of the present invention.

DESCRIPTION OF THE PREFERRED EMBODIMENTS

Figure 1:
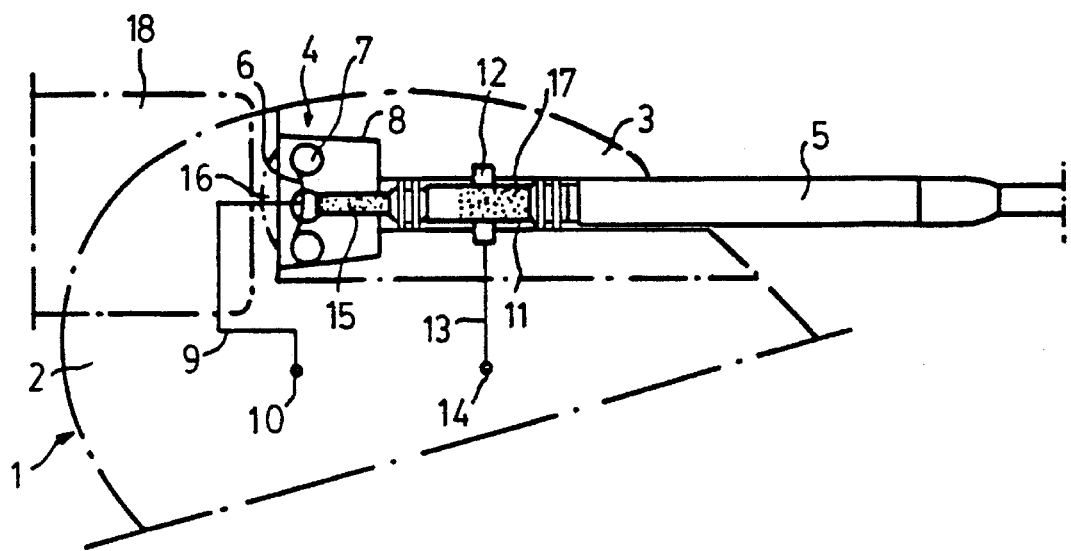
FIGS. 1 and 2 are side schematic views of a connector part of an apparatus for emitting electrical pulses, with a fixing device constructed in accordance with the principles of the present invention shown in cross-section, the spring element of the affixing device being respectively shown in first and second positions in the figures.

In FIG. 1, the outline of an apparatus for emitting electrical pulses, in the form of a pacemaker 1, is shown in dashed lines. The outlined portion includes a stimulation pulse generator part 2 and a connector part 3. An affixing device 4 constructed in accordance with the principles of the present invention is contained in the connector part 3. The affixing device 4 is arranged for affixing the pin-like proximal end of an electrode cable 5 for a pacemaker electrode. The affixing device 4 includes a spring element 6, in the form of a convex, substantially spherical disk. The spring element or disk 6 is provided with spherical clamping elements 7, which are uniformly distributed around the edge of the disk 6. The affixing device 4 is contained in a hood 8, having the shape of a truncated cone, whose base is attached to the stimulation pulse generator part 2. The largest diameter of the hood 8 is only slightly larger than the outer dimension of the disk 6 when the disk assumes an extended, first position described below. The slope of the truncated cone, i.e., the orientation of the inner wall of the hood 8, is selected so that it roughly follows a curve describing the peripheral surface of the affixing element 4 when the affixing element 4 moves from the extended, first position to a second, clamping position. The hood 8 serves to hold the loosely arranged spring element 8 and the spherical clamping elements 7 inside the hood 8, so that the spring element 6 is always substantially perpendicular to the longitudinal axis of the proximal end of the electrode cable 5 introduced into the connector part 3. The affixing device 4 is made of an electrically conductive material, and is electrically coupled via a conductor 9 to an electrically contact 10 in the stimulation pulse generating electronics contained within stimulation generator part 2. If the pacemaker electrode is bipolar, a contact part 12, coupled to an electrical contact 14 in the stimulation pulse generator in the stimulation pulse generator part 2, is also arranged in a channel 11 of the connector part 3. Coupling the contacts 10 and 14 is achieved in a known manner, and will therefore not be shown or described in further detail.

Figure 2:
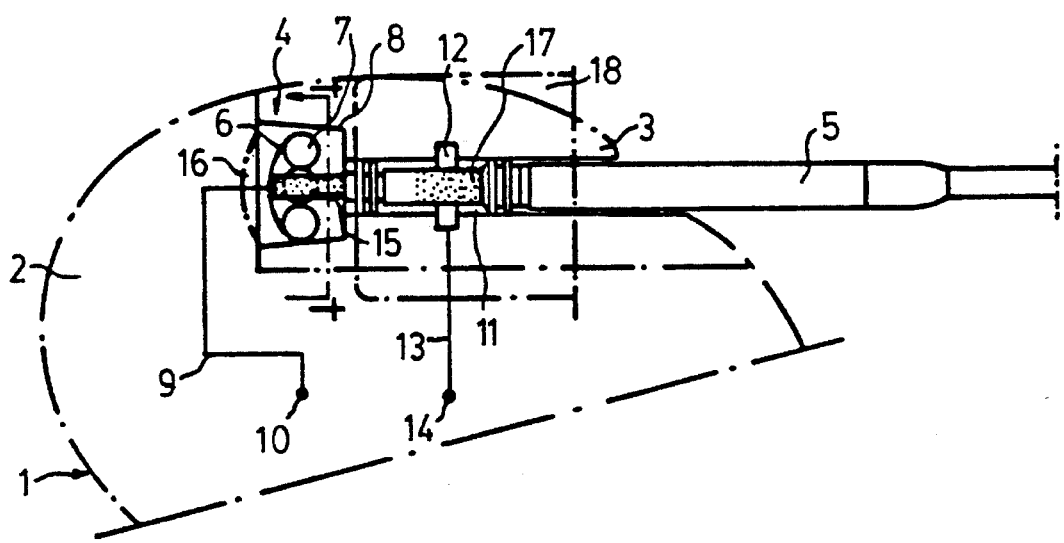

Before the proximal end of the electrode cable 5 is affixed, the spring element 6, in a manner described below, is brought into a first position in which the bulge of the disk faces the channel 11, and in which the spherical clamping elements 7 assume the position shown in FIG. 1. In this first position, the pin-like proximal end of the electrode cable 5 is permitted to pass the clamping elements 7. The end of the electrode cable 5 can then be advanced through the channel into the hood 8, so that the pin 15 on the electrode and presses against the bulge of the disk 6. When the cable end is advanced farther the pin 15 presses against the bulge so that the disk 6 is extended, and the disk 6 snaps into a second position wherein the bulge faces away from the pin 15. In this second position, the clamping elements 7 engage and affix the pin 15, and thus the electrode cable 5, in the pacemaker 1, as shown in FIG. 2. When the disk 6 snaps from the first position into the second position, it emits an audible clicking sound, indicating that the electrode cable 5 has become affixed to the pacemaker 1. In order to permit the bulge of the disk 6 to be shiftable from the first position to the second position by means of the pin 15 in the manner described above, the base of the hood 8 is provided with a cavity 16 which conforms to the position and shape of the bulge when the bulge faces away from the pin 15. This bulge is pressed into this cavity 16 by the end of the pin 15. The cavity 16 is shown with a dashed line. The pin 15, which is electrically conductive and is coupled, for example, to the tip of the pacemaker electrode via a conductor (not shown) in the electrode cable 5, is now electrically coupled to the stimulation pulse generating electronics in the stimulation pulse generator part 2. The contact part 12 surrounds a contact surface 17 on the electrode cable 5, which is conducted via a conductor (not shown) in the electrode cable 5 to, for example, an indifferent electrode.

The spring element or disk 6 and/or the clamping elements 7 are made of a material susceptive to magnet force generated by a magnet 18. For explantation of the pacemaker 1 or explantation of the pacemaker electrode 5, for which purpose it is necessary to separate the pacemaker 1 from the electrode cable 5, the magnet 18 is placed in the position indicated by the dashed line in FIG. 1, just behind the affixing device 4 as "seen" from the side of the connector part 3 at which the electrode cable 5 is introduced. The magnetic force generated by the magnet 18 attracts the spherical clamping elements 7, thereby forcing the spring element or disk 6 from its second position, shown in FIG. 2, into its first position shown in FIG. 1. An audible clicking sound is again emitted, indicating that the pin 15 at the end of the electrode cable 5 has become released from the affixing device 4, so that the electrode cable 5 can be withdrawn from the pacemaker 1.

Instead of a procedure wherein the bulge of a disk 6 is pressed by means of the pin 15 from the first position to the second position, this change in position can alternatively be achieved by the magnet 18. This is accomplished by placing the magnet 18 against the pacemaker stimulation pulse generator part 2 just in front of the affixing device 4, along side and parallel to the electrode cable 5 loosely introduced into the connector part 3. The magnetic force generated by the magnet 18 attracts the spherical clamping elements 7, causing the bulge of the disk 6 to move from the first position to the second position, shown in FIG. 2, in which the clamping elements 7 engage the end of the electrode cable 5. The cavity 16 is not required when the magnet 18 is used for affixing the end of the electrode cable 5.

As shown in FIG. 3, the spherical clamping elements 7 are uniformly distributed around the spring element at the edge (periphery) of the disk 6. The number of clamping elements 7 can be more or less than the number shown in FIG. 3. In FIG. 4, an embodiment of the spring element 6 is shown having a non-spherical, cruciate configuration.

Figure 6:
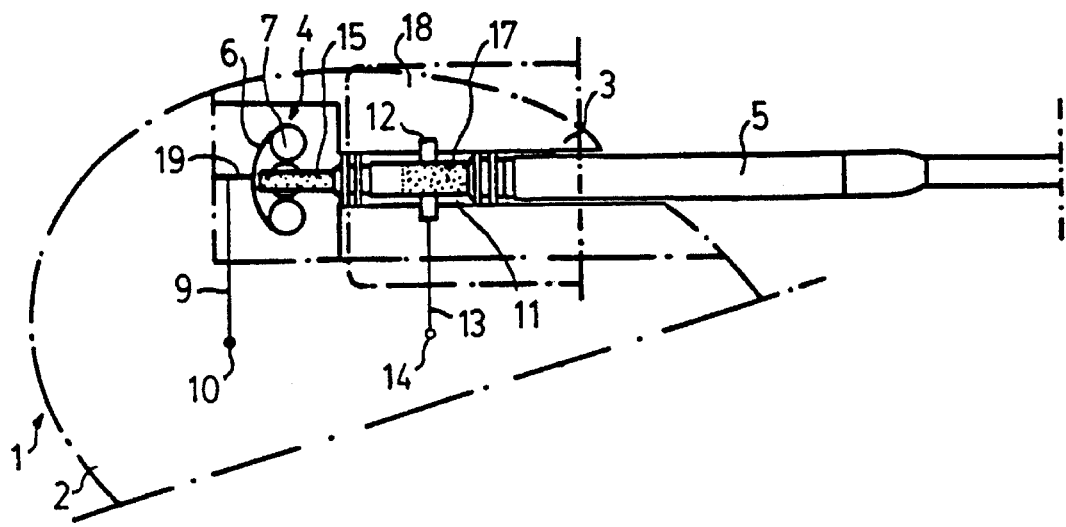

The embodiment shown in FIG. 5 shows that the affixing device 4 with the spring element 6 and the clamping elements 7 need not necessarily be arranged in the hood 8 shown in FIGS. 1 and 2. The spring element 6 can instead be permanently connected to, for example, the stimulation pulse generator part 2, by means of a pin-like holder 19. The pin-like holder 19 is attached to a central area at a side of the spring element 16 which faces the stimulation pulse generator part 2. Application of the holder 19 against the disk 6 is also shown in FIG. 3. The length of the holder 19 is selected so that the spring element 6, even in the first position, i.e., the position at which the bulge of the spring element or disk 6 faces the proximal end of the electrode cable 5, does not touch the stimulation pulse generator part 2 in which the holder 19 is attached. In the embodiment of the affixing 4 shown in FIGS. 5 and 6, the aforementioned first and second positions are achieved exclusively by means of the magnet 18, as described in the alternative version in conjunction with FIGS. 1 and 2. When the spherical clamping elements 7 shift from the first position to the second position, or vice-versa, the aforementioned audible clicking sound is emitted, indicating that the electrode cable 5 has either become affixed to, or released from, the affixing device 4.

Figure 7:
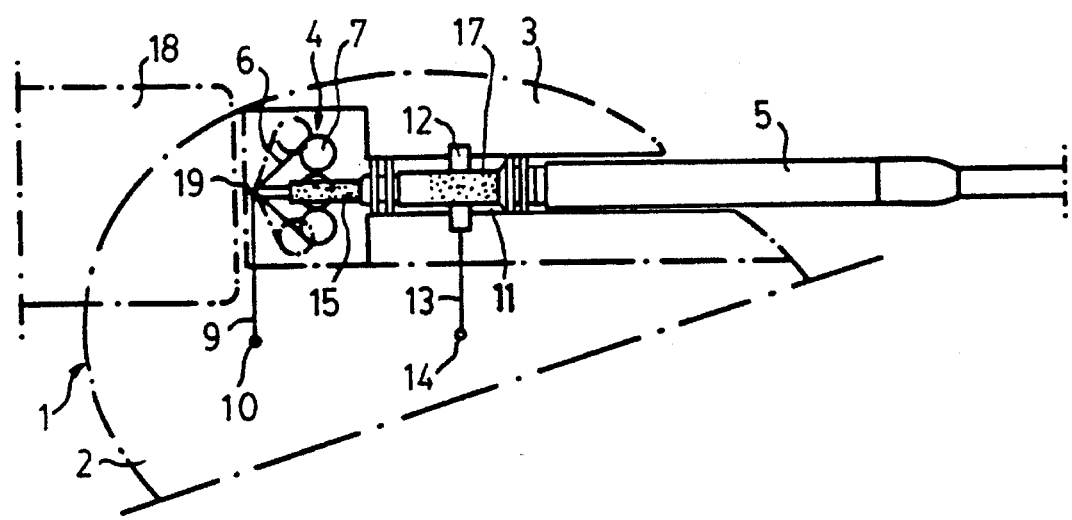

In the embodiment of FIG. 7, an affixing device 4 is shown having a spring element 6 which differs from the form described in the previously-discussed embodiment. In the embodiment of FIG. 7, the spring element 6 has a V-shaped profile, as seen from the side. When viewed from the front, the spring element can have the shape shown in FIG. 4. Before an electrode cable 5 is introduced into the connector part 3, the magnet 18 is placed on the pacemaker 1 immediately behind the affixing device 4, as shown in FIG. 7, causing the clamping elements 7 and the spring element 6 to be moved from a position wherein the clamping elements touch, or nearly touch, each other, toward the magnet 18, as illustrated by the dashed-line version of the affixing device 4. When the clamping elements 7 are in this position, the pin 15 at the proximal end of the electrode cable 5 can be inserted into the affixing device 4, so that it passes the clamping elements 7. The magnet 18 is then removed, whereupon the clamping elements 7, by virtue of the bias of the spring element 6, attempt to resume their original positions, thereby affixing the pin 15. When the electrode cable 5 is to be detached from the pacemaker 1, the magnet 18 is re-applied in the described manner, thereby detaching the clamping elements 7 from the pin 15. The spring element 6 can be attached directly to the stimulation pulse generator part 2, or by means of a pin-like holder 19. The affixing device 4 is devised so that the magnet 18 can act on the spring element 6 or on the clamping elements 7 only when the magnet 18 is oriented relative to the stimulation pulse generator part 2 in the described manner. The affixing device 4 is not affected after the pacemaker 1 has been implanted in a patient if a magnet were then to be applied against the chest or stomach of the patient over the pacemaker 1, because the distance between the affixing device 4 and the magnet 18 would then be too large. This permits the physician to use the same magnet both for attaching and detaching the electrode cable 5 and for changing pacemaker functions, while ensuring that the conventional magnets which have heretofore been employed for altering pacemaker functions are incapable of inadvertently releasing the affixing device 4.

The affixing device 4 can clearly be used as well in conjunction with a defibrillation apparatus. The advantage of an affixing device constructed in accordance with the principles of the present invention is that the connector part 3 can be completely integrated into the pacemaker housing so that the housing can enclose the connector part 3 as well as the stimulation pulse generator part 2. This permits the pacemaker can to enclose both of these parts, thereby providing a simpler design for manufacturing in comparison to standard manufacturing techniques wherein the connector part is provided as a separate part and must be attached to the pacemaker housing, which in a conventional design contains only the stimulation pulse generator part. The result of the invention is a pacemaker which is very effectively sealed against the entry of body fluids. In addition, rapid, safe and distinct affixing and detachment of the electrode cable to and from the pacemaker 1 is achieved by the invention, with each operation being acoustically confirmed by means of a click. The clamping elements described herein need not necessarily be spherical, but may have other configurations, such as a conical shape wherein the tip of the cone engages the pin at the end of the electrode cable.

Although further modifications and changes may be suggested by those skilled in the art, it is the intention of the inventor to embody within the patent warranted hereon all changes and modifications as reasonably and properly come within the scope of his contribution to the art.

I claim as my invention:

1. A device for affixing an electrode cable to an apparatus for emitting electrical pulses, said apparatus having a connector part and said electrode cable having a pin-shape proximal end having a longitudinal axis adapted to be received in said connector part and comprising:

a spring element extending substantially perpendicularly to said longitudinal axis of said proximal end of said electrode cable;

a plurality of clamping elements carried by said spring element; and said spring element being movable between a first position at which said spring element holds all of said clamping elements at respective first locations to permit said proximal end of said electrode cable to pass said clamping elements and being activatable into a second position by interaction with said electrode cable at which said spring element holds all of said clamping elements at respective second locations so as to engage and affix said proximal end of said electrode cable.

2. A device as claimed in claim 1 wherein said spring element comprises a convex disk having a bulge, said bulge in said first position facing said proximal end of said electrode cable and in said second position facing away from said proximal end of said electrode cable.

3. A device as claimed in claim 1 wherein said spring element has a V-shaped profile and wherein said clamping elements in said second position have an inner diameter which is less than an outer diameter of said proximal end of said electrode cable.

4. A device as claimed in claim 1 wherein said clamping elements are uniformly distributed around an edge of said spring element relative to said proximal end of said electrode cable.

5. A device as claimed in claim 1 wherein said clamping elements are spherical.

6. A device as claimed in claim 1 further comprising means for electrically coupling said clamping elements to an electrical contact in said apparatus.

7. A device as claimed in claim 1 wherein said spring element consists of magnetically susceptible material.

8. A device as claimed in claim 1 wherein said clamping elements consist of magnetically susceptible material.

9. A device as claimed in claim 1 wherein said spring element and said clamping elements consist of magnetically susceptible material.

10. A device as claimed in claim 1 further comprising a hood having the shape of a truncated cone and having a base adapted for attachment to said apparatus, said hood having a maximum inner diameter slightly larger than an outer dimension of said spring element in said first position, said hood containing said spring element and said clamping elements, and said hood having an inner wall roughly following a curve described by a peripheral surface of said clamping elements when said spring element moves between said first and second positions.

11. A device as claimed in claim 1 wherein said spring element has a central area facing said apparatus and adapted to be permanently connected to said apparatus.

* * * * *